(12) United States Patent
Matthews

(10) Patent No.: US 10,249,064 B2
(45) Date of Patent: Apr. 2, 2019

(54) MOTION ESTIMATION METHOD AND APPARATUS

(71) Applicant: Toshiba Medical Systems Corporation, Otawara-shi (JP)

(72) Inventor: James Matthews, Edinburgh (GB)

(73) Assignee: TOSHIBA MEDICAL SYSTEMS CORPORATION, Otawara-shi (JP)

(*) Notice: Subject to any disclaimer, the term of this patent is extended or adjusted under 35 U.S.C. 154(b) by 148 days.

(21) Appl. No.: 15/225,947

(22) Filed: Aug. 2, 2016

(65) Prior Publication Data

US 2018/0040145 A1    Feb. 8, 2018

(51) Int. Cl.
*G06K 9/00* (2006.01)
*G06T 11/00* (2006.01)
(Continued)

(52) U.S. Cl.
CPC .......... *G06T 11/005* (2013.01); *A61B 6/0407* (2013.01); *A61B 6/5205* (2013.01);
(Continued)

(58) Field of Classification Search
CPC ............ G06T 2211/412; G06T 11/005; G06T 11/006; G06T 2207/10081;
(Continued)

(56) References Cited

U.S. PATENT DOCUMENTS

| | | |
|---|---|---|
| 8,638,999 B2 | 1/2014 | Xu et al. |
| 9,008,401 B1 | 4/2015 | Katsevich et al. |

(Continued)

FOREIGN PATENT DOCUMENTS

| | | |
|---|---|---|
| JP | 2007-526069 A | 9/2007 |
| JP | 2009-240723 A | 10/2009 |

(Continued)

OTHER PUBLICATIONS

Terry Peters, "CT Image Reconstruction—AAPM," Roberts Research Institute, https://www.aapm.org/meetings/02AM/pdf/8372-23331.pdf, 49 pages.

(Continued)

*Primary Examiner* — Li Liu
(74) *Attorney, Agent, or Firm* — Oblon, McClelland, Maier & Neustadt, L.L.P.

(57) ABSTRACT

A medical imaging data processing apparatus comprises processing circuitry configured to: obtain a first data set representative of at least some measurements of a measurement volume obtained by rotation of a medical scanner relative to the measurement volume during a first scanning time period; obtain a second data set representative of at least some measurements of the measurement volume obtained by rotation of the medical scanner relative to the measurement volume during a second scanning time period that overlaps the first scanning time period; and perform a procedure to obtain an estimate of motion between the first scanning time period and second scanning time period based on the first data set and second data set; wherein the obtaining is such as to exclude from the first data set and from the second data set at least some of the data representative of said measurements obtained during an overlap between the first scanning time period and second scanning time period; and wherein a data set representative of measurements obtained during at least one of the first scanning time period and second scanning time period is suitable for use in reconstructing a medical imaging data set representative of at least part of the measurement volume.

20 Claims, 5 Drawing Sheets

(51) Int. Cl.
*A61B 6/04* (2006.01)
*A61B 6/00* (2006.01)
*A61B 6/03* (2006.01)

(52) U.S. Cl.
CPC .......... *A61B 6/5264* (2013.01); *G06T 11/006* (2013.01); *A61B 6/032* (2013.01); *A61B 6/503* (2013.01); *G06T 2207/10081* (2013.01); *G06T 2207/30048* (2013.01)

(58) Field of Classification Search
CPC ......... G06T 2207/30048; G06T 11/003; G06T 2207/30004; G06T 2211/428; G06T 7/174; A61B 6/5264; A61B 5/1128; A61B 6/03; G06K 9/00
See application file for complete search history.

(56) References Cited

U.S. PATENT DOCUMENTS

| | | | |
|---|---|---|---|
| 9,959,631 B2* | 5/2018 | Ra | A61B 6/032 |
| 2007/0183639 A1* | 8/2007 | Kohler | G06T 11/006 382/131 |
| 2010/0121183 A1* | 5/2010 | Taguchi | A61B 6/5264 600/427 |
| 2010/0208962 A1* | 8/2010 | Roessl | G06T 11/005 382/131 |
| 2011/0142313 A1* | 6/2011 | Pack | G06T 11/005 382/131 |
| 2011/0206258 A1 | 8/2011 | Chen et al. | |
| 2011/0263981 A1* | 10/2011 | Hamilton | G06T 7/2033 600/443 |
| 2013/0051643 A1* | 2/2013 | Jackson | G06T 11/006 382/131 |
| 2016/0110874 A1 | 4/2016 | Matthews et al. | |
| 2016/0171724 A1* | 6/2016 | Nett | G06T 11/006 382/131 |
| 2016/0180553 A1* | 6/2016 | Edic | A61B 6/032 382/107 |
| 2016/0225170 A1* | 8/2016 | Rifu | G06T 11/005 |
| 2017/0258432 A1* | 9/2017 | Choi | A61B 6/032 |
| 2017/0340304 A1* | 11/2017 | Qiulin | A61B 6/5264 |

FOREIGN PATENT DOCUMENTS

| | | |
|---|---|---|
| JP | 2011-172926 A | 9/2011 |
| JP | 2012-152446 A | 8/2012 |

OTHER PUBLICATIONS

Qiulin Tang, et al. "Motion estimation and compensation for coronary artery and myocardium in cardiac CT," Medical Imaging 2015: Physics of Medical Imaging, Proc. of SPIE, vol. 9412, 94120Q, pp. 94120Q-1 to 94120Q-10.

Martina Chantal de Knegt, "Coronary Artery Adaptive Motion Correction Software," Toshiba Visions Magazine, Jul. 2015, article on pp. 63-65, 68 total pages.

Jim Piper, et al., "Objective Evaluation of the Correction by Non-Rigid Registration of Abdominal Organ Motion in Low-Dose 4D Dynamic Contrast-Enhanced CT," Physics in Medicine and Biology, vol. 57(6), 2012, pp. 1-17.

William R. Crum, et al., "Information Theoretic Similarity Measures in Non-Rigid Registration," Proceedings of IPMI'2003, 10 pages.

Qiulin Tang, et al. "A combined local and global motion estimation and compensation method for cardiac CT," Proc. SPIE 9033, Medical Imaging: physics of Medical Imaging, 903304, Mar. 19, 2014, 6 pages.

* cited by examiner

MOTION ESTIMATION METHOD AND APPARATUS

FIELD

The present invention relates to a method of estimating motion in measurement data obtained by a medical scanner, for example estimating motion in measurement data by registering partial reconstructions of measurement data.

BACKGROUND

Image quality in CT scans of the heart may be affected by heart motion. Motion of the heart within the duration of a cardiac CT scan capture may result in the presence of motion artifacts in images derived from the cardiac CT scan.

FIG. 1 shows an image derived from a CT scan of the heart. Ellipses 2 indicate vessels with severe motion artifacts. Normally, in an image derived from a scan without significant motion artifacts, it may be expected that vessels would appear as approximately circular. However in FIG. 1 the vessels within ellipses 2 are significantly distorted.

Heart motion may particularly affect image quality in scans that are taken at high heart rates, for example heart rates over 60 beats per minute (bpm). Advanced scanners may obtain good image quality with moderately high heart rates, but may still see decreased quality at higher heart rates.

Scanners with a fast rotation may produce better results than scanners with a slower rotation, but motion artifacts may still be an issue even when fast rotation is used.

For some patients, drugs such as beta-blockers may be administered to slow the patient's heart rate, for example to slow the patient's heart rate below 60 beats per minute. However, beta-blockers may be contraindicated in some patients. Some patients may be unable to take beta-blockers, for example due to medical conditions.

It is known to estimate heart motion by comparing image data that is representative of different points in time, to determine motion that has occurred between the different time points.

BRIEF DESCRIPTION OF THE DRAWINGS

Embodiments are now described, by way of non-limiting example, and are illustrated in the following figures, in which:—

DETAILED DESCRIPTION

Certain embodiments provide a medical imaging data processing apparatus, comprising processing circuitry configured to: obtain a first data set representative of at least some measurements of a measurement volume obtained by rotation of a medical scanner relative to the measurement volume during a first scanning time period; obtain a second data set representative of at least some measurements of the measurement volume obtained by rotation of the medical scanner relative to the measurement volume during a second scanning time period that overlaps the first scanning time period; and perform a procedure to obtain an estimate of motion between the first scanning time period and second scanning time period based on the first data set and second data set; wherein the obtaining is such as to exclude from the first data set and from the second data set at least some of the data representative of said measurements obtained during an overlap between the first scanning time period and second scanning time period; and wherein a data set representative of measurements obtained during at least one of the first scanning time period and second scanning time period is suitable for use in reconstructing a medical imaging data set representative of at least part of the measurement volume.

Certain embodiments provide a medical imaging data processing method, comprising: obtaining a first data set representative of at least some measurements of a measurement volume obtained by rotation of a medical scanner relative to the measurement volume during a first scanning time period; obtaining a second data set representative of at least some measurements of the measurement volume obtained by rotation of the medical scanner relative to the measurement volume during a second scanning time period that overlaps the first scanning time period; and performing a procedure to obtain an estimate of motion between the first scanning time period and second scanning time period based on the first data set and second data set; wherein the obtaining is such as to exclude from the first data set and from the second data set at least some of the data representative of said measurements obtained during an overlap between the first scanning time period and second scanning time period; and wherein a data set representative of measurements obtained during at least one of the first scanning time period and second scanning time period is suitable for use in reconstructing a medical imaging data set representative of at least part of the measurement volume.

Figure 2:
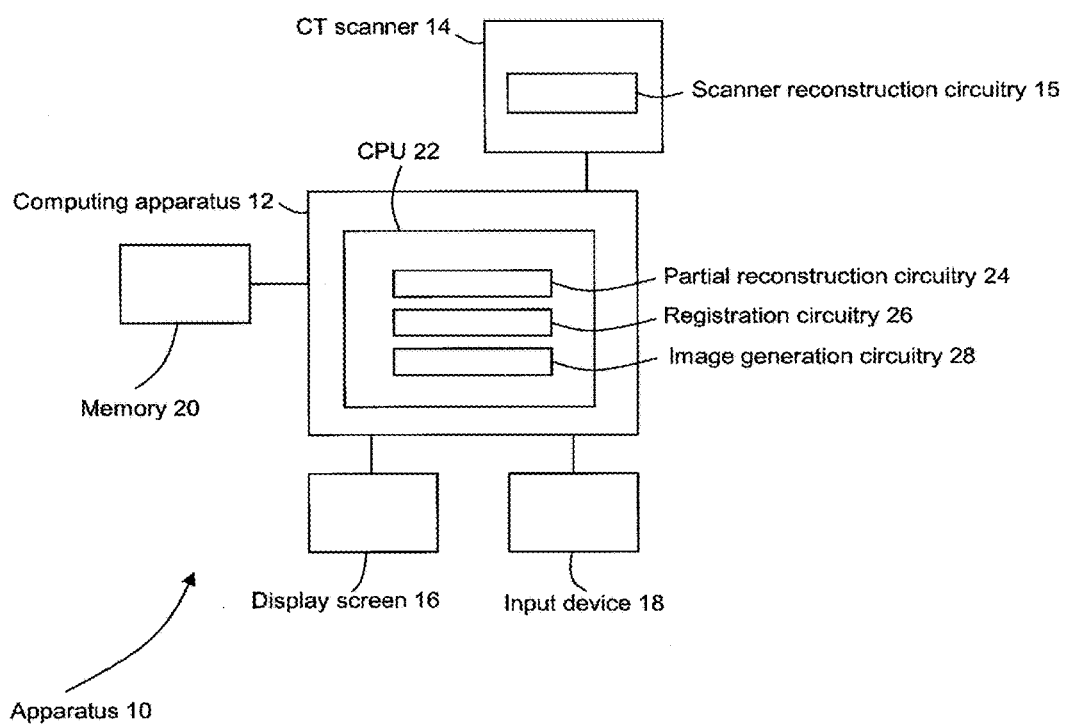
FIG. 2 is a schematic illustration of an apparatus according to an embodiment.

An imaging data processing apparatus 10 according to an embodiment is illustrated schematically in FIG. 2. The imaging data processing apparatus 10 comprises a computing apparatus 12, for example, a personal computer (PC) or workstation, which is connected to a CT scanner 14, one or more display screens 16 and an input device or devices 18, such as a computer keyboard, mouse or trackball.

The CT scanner 14 may be any CT scanner that is configured to obtain two-dimensional or three-dimensional CT scan data that is representative of a region of a patient or other subject. In the present embodiment, the region is an anatomical region comprising the heart. In other embodiments, the region may be any appropriate region. The region may comprise the brain. The region may comprise the abdomen. The region may comprise any appropriate vessel (for example, the coronary arteries) or organ (for example, the lung or liver). The region of the patient that is scanned may be referred to as a measurement volume.

The CT scanner 14 is configured to scan the region of the patient using an X-ray source and receiver mounted on a gantry. In some embodiments, a scan protocol used is a continuous volume acquisition. The gantry performs a full 360° rotation around the patient in a rotation time, which in the present embodiment is 275 ms. In some circumstances, a full rotation may be completed within a single heartbeat of the patient.

In some embodiments, each full rotation around the patient provides CT scan data that is representative of an axial slice of the region of the patient. In other embodiments, the CT scanner 14 is a multi-slice scanner configured to capture a plurality of slices in a single rotation.

In alternative embodiments, the CT scanner 14 may be replaced or supplemented by a scanner in any other imaging modality, for example a cone-beam CT scanner, MRI (magnetic resonance imaging) scanner, X-ray scanner, PET scanner (positron emission tomography), SPECT (single photon emission computed tomography) scanner, ultrasound scanner, or hybrid scanner (for example, CT-MR or CT-PET scanner).

In the description below, the term scan data set (for example, CT scan data set) is used to refer to raw (unreconstructed) data as may be received from a scanner. CT scan data may be representative of measurements obtained by the scanner during a CT scan, for example voltage data that is obtained by the scanner during the CT scan. A CT scan data set may comprise data that is representative of one or more axial slices. In some circumstances, a CT scan data set may be referred to as a sinogram.

A CT scan data set may comprise a plurality of subsets of data, each corresponding to a different time during a scan and therefore to a different scan angle.

In the present embodiment, CT scanner 14 comprises scanner reconstruction circuitry 15 which is configured to reconstruct CT scan data to obtain imaging data. By reconstruction, the scanner reconstruction circuitry 15 transforms the raw CT data into imaging data that comprises voxel intensities that are representative of the attenuation of X-rays at different points in space.

In the description below, the term imaging data set is used to refer to reconstructed data (which may be also referred to as imaging data). An imaging data set may comprise, for example, an array of voxels and associated intensities, with each voxel being representative of a corresponding location in the measurement volume. An imaging data set may be used to generate an image of the measurement volume, for example for display.

The CT scanner 14 may reconstruct CT scan data to obtain imaging data using any suitable method, for example filtered back-projection.

In the present embodiment, the CT scanner 14 is configured to reconstruct three imaging data sets for each axial slice of the CT scan data. In other embodiments, the CT scanner is configured to reconstruct a different number of imaging data sets for each axial slice of the CT scan data.

For each axial slice, CT scan data is obtained for a full 360° rotation of the X-ray source. Each of the three imaging data sets for a given slice is reconstructed using a respective portion of the CT scan data for that slice. Each portion comprises CT scan data from at least half of the rotation, i.e. CT scan data from at least 180° of rotation. Each portion is offset in time, and is therefore also offset in rotation angle. For example, the three imaging data sets may be offset in time by a time corresponding to one-sixth of a rotation by the X-ray source (60° of rotation).

Data from at least 180° of rotation may be reconstructed to provide a complete reconstruction, which may be an imaging data set corresponding to an image of the entire axial slice. In some embodiments, data from an angular range of 180° plus a width of a fan beam of the scanner is reconstructed to provide a complete reconstruction. In some embodiments, references below to an angular range of 180° may be replaced with a range of 180° plus a width of a fan beam of the scanner.

In some circumstances, data from 180° of rotation may be used for parallel projections. Real CT scanners may be fan beam scanners and may use a larger range of rotational angles in reconstruction. However, some motion estimation methods and/or motion compensation methods may ignore the fan beam nature of the CT scanner and assume a parallel projection. For example, since cardiac scans may have a small field of view, the fan beam angle may be fairly small and may be close enough to parallel that good results may be achieved using parallel projection.

Each of the three imaging data sets may comprise a complete reconstruction of the axial slice, with each full reconstruction being obtained using measurements from a different range of rotation angles. Three separate images of the same axial slice may be provided, each image corresponding to a different scanning time period.

If no motion were to occur in the measurement volume during the rotation, it may be expected that each of the three imaging data sets may be substantially identical. However, the presence of motion may cause differences between the imaging data sets obtained at different times (and at different angles).

Figure 1:
FIG. 1 is a cardiac CT image exhibiting motion artifacts.

Each of the imaging data sets may comprise motion artifacts, for example motion artifacts similar to those shown in FIG. 1. The motion artifacts in an imaging data set may result from motion occurring during a scanning time period in which the relevant portion of the CT scan data was acquired. Motion may occur on a timescale of less than half a rotation of the scanner. For example, a shape and/or position of at least part of the heart may change between the acquisition of measurements for a first angle and the acquisition of measurements for a second angle that offset from the first angle by less than 180°.

Figure 3:
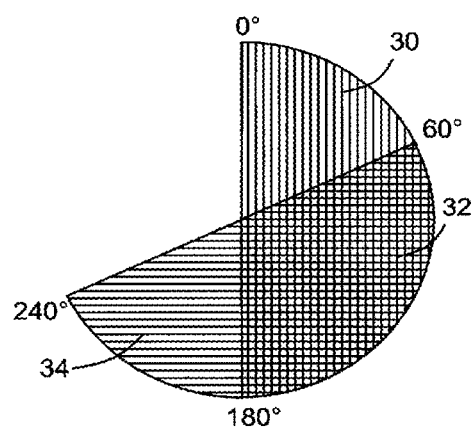
FIG. 3 is a schematic illustration of ranges of rotation angles corresponding to different images.

FIG. 3 is a schematic illustration of ranges of gantry rotation angles from which two imaging data sets A, T representative of two images of the same slice are reconstructed. A range of angles for a third imaging data set, B, representative of a third image of the same slice is not shown in FIG. 3 for clarity. First imaging data set A is reconstructed from measurements for a range of angles from 0° to 180°, which encompasses regions 30 and 32 of FIG. 3. The range of angles used to reconstruct first imaging data set A is represented using vertical hatching. Second imaging data set T is reconstructed from measurements for a range of angles from 60° to 240°, which encompasses regions 32 and 34 of FIG. 3. The range of angles used to reconstruct first imaging data set A is represented using horizontal hatching. It may be seen that measurements for a range of angles from 60° to 180° are used both in the reconstruction of first imaging data set A and in the reconstruction of second imaging data set T. In the embodiment of FIG. 3, third imaging data set B is reconstructed from measurements for a range of angles from 120° to 300° (not shown).

In the present embodiment, imaging data sets reconstructed by the CT scanner 14 (for example, A, T and B) are stored in memory 20 and subsequently provided to computing apparatus 12. In an alternative embodiment, imaging data sets are supplied from a remote data store (not shown) which may form part of a Picture Archiving and Communication System (PACS). The memory 20 or remote data store may comprise any suitable form of memory storage.

Computing apparatus 12 provides a processing resource for automatically or semi-automatically processing imaging data sets, and comprises a central processing unit (CPU) 22. In the present embodiment, the computing apparatus 12 includes partial reconstruction circuitry 24, registration circuitry 26 and image generation circuitry 28.

In the present embodiment, the partial reconstruction circuitry 24, registration circuitry 26, and image generation circuitry 28 are each implemented in computing apparatus 12 by means of a computer program having computer-readable instructions that are executable to perform the method of the embodiment. For example, the partial reconstruction circuitry 24, registration circuitry 26, and image generation circuitry 28 may each be implemented as a respective computer program or algorithm that is executable by the computing apparatus 12, for example by the CPU 22. However, in other embodiments, the various units may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 2 for clarity.

The system of FIG. 2 is configured to perform the method of an embodiment as described below with reference to FIG. 4. The method of FIG. 4 comprises a motion estimation and motion compensated reconstruction method. Although three imaging data sets A, T, B were described above, for simplicity the method of FIG. 4 is described below for an embodiment in which a pair of imaging data sets R, T are used.

In some embodiments, motion is estimated from two volumes R, T, producing a single warp field. The warp field may be considered to be a motion estimate, and may be used in reconstruction. In some embodiments, three imaging data sets are used and motion estimation (for example, using the method described below with reference to FIG. 4) is run twice. Two warp fields are produced, which are fed into a reconstruction stage. In other embodiments, any appropriate number of imaging data sets and any appropriate number of motion estimations may be used.

At stage 40 of the flow chart of FIG. 3, the partial reconstruction circuitry 24 receives a first imaging data set R from the memory 20. The first imaging data set has been reconstructed by the CT scanner 14 from data representative of CT measurements obtained by the CT scanner over the duration of a first scanning time period. In the first scanning time period, the gantry rotates through a first range of rotation angles (for example, 0° to 180°). In other embodiments, first imaging data set R may be received from the CT scanner 14 or from a data store, for example a remote data store.

First imaging data set R is representative of an anatomical region of a patient, which in this embodiment comprises the patient's heart. In this embodiment, first imaging data set R is representative of an axial slice through the patient's heart. First imaging data set R may be considered to be a full reconstruction for the axial slice to which it corresponds.

At stage 42 (which may be concurrent with stage 40), the partial reconstruction circuitry 24 receives a second imaging data set T from the CT scanner 14. Second imaging data set T is representative of the same axial slice of the same region of the patient as first imaging data set R. Second imaging data set T has been reconstructed by the CT scanner 14 from data representative of CT measurements obtained by the CT scanner over the duration of a second scanning time period. During the second scanning time period, the gantry rotates through a second range of rotation angles (for example, 60° to 240°).

The first scanning time period and second scanning time period overlap. The second range of rotation angles overlaps with the first range of rotation angles.

Turning once again to FIG. 3, in one embodiment the first imaging data set R is reconstructed using measurements acquired for an angular range from 0° to 180°, which corresponds to regions 30 and 32 of FIG. 3. The second imaging data set T is reconstructed using measurements acquired for an angular range from 60° to 240°, which corresponds to regions 32 and 34 of FIG. 3. Data from the range of angles from 60° to 180° (region 34) is common to imaging data sets R and T.

Figure 4:
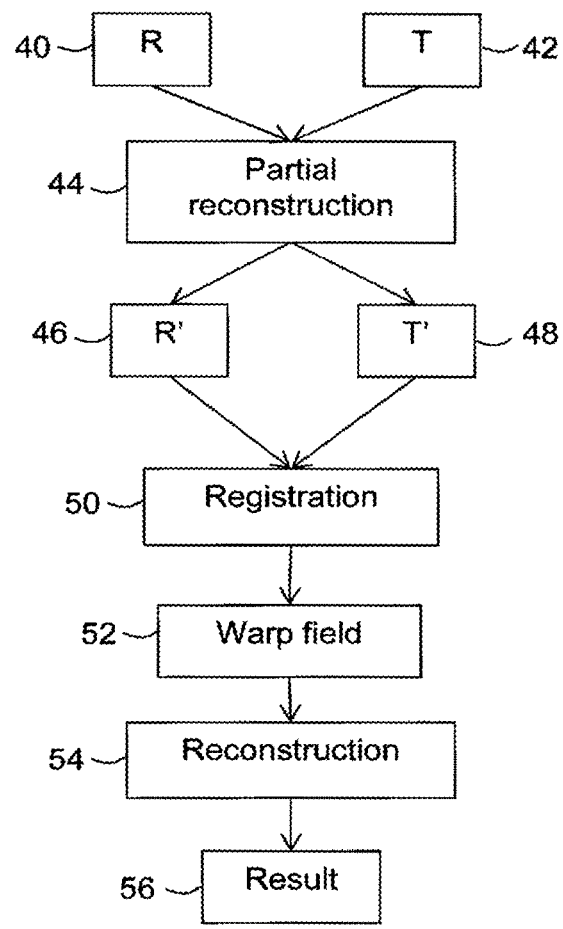
FIG. 4 is a flow chart illustrating in overview a method of an embodiment.

At stage 44 of the flow chart of FIG. 4, the partial reconstruction circuitry 24 uses the first imaging data set R to obtain a first partial reconstruction imaging data set R' that is reconstructed from data representative of measurements for the range of angles represented by region 30 of FIG. 3 (i.e., 0° to 60°). The partial reconstruction circuitry 24 uses the second imaging data set T to obtain a second partial reconstruction imaging data set T' that is reconstructed from data representative of measurements for the range of angles represented by region 34 of FIG. 3 (i.e., 180° to 240°). Data representative of measurement for the range of angles represented by region 32 of FIG. 3 (i.e., 60° to 180°) is excluded from the reconstruction of first partial reconstruction imaging data set R' and second partial reconstruction imaging data set T'.

Figure 5:
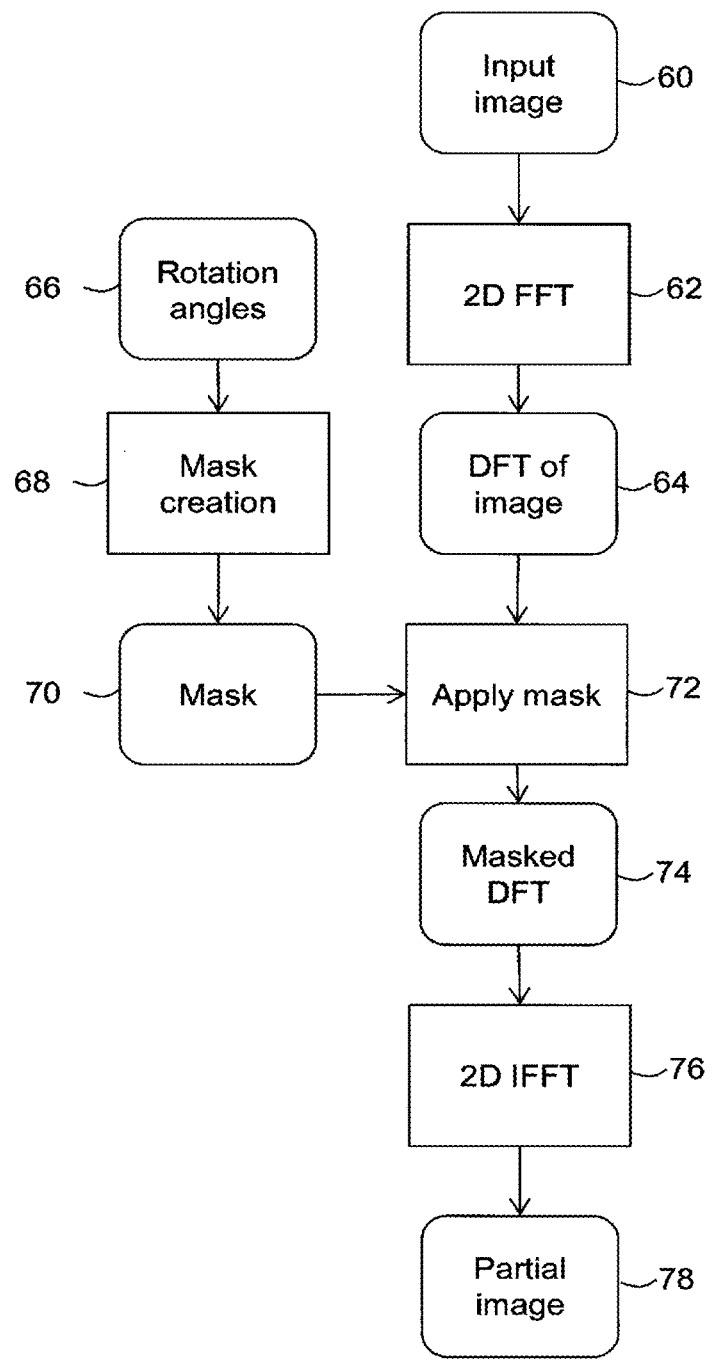
FIG. 5 is a flow chart illustrating in overview a method of obtaining partial reconstructions.

FIG. 5 is a flow chart illustrating in overview one method of obtaining a partial reconstruction (for example, R') from a complete reconstruction (for example, R).

In the present embodiment, the partial reconstruction circuitry 24 has obtained imaging data set R (represented as input image 60 in FIG. 5) from the CT scanner 14 at stage 40 of FIG. 4. In the present embodiment, the partial reconstruction circuitry 24 does not have access to the CT scan data from which the CT scanner reconstructed imaging data set R.

At stage 62, the partial reconstruction circuitry 24 processes the imaging data set R to obtain data that is representative of measurements obtained by the scanner during the first scanning time period. In the present embodiment, the partial reconstruction circuitry 24 processes the imaging data set R by performing a two-dimensional fast Fourier transform (FFT) to produce a discrete Fourier transform (DFT) 64 of the imaging data set R. In other embodiments, any suitable processing method may be used.

Due to the central slice theorem, radial angles of the DFT 64 may correspond to gantry angles. Data that lies along a line passing through the origin of the DFT 64 at a given radial angle may be representative of measurement data acquired at a corresponding gantry angle. The DFT 64 is a transformed image slice that is capable of being created either by taking a 2D DFT of the reconstructed image (as performed at stage 62) or by taking a one-dimensional DFT of each line of the sinogram (raw CT scan data) and overlaying the 1D DFT results at appropriate radial angles through the centre of an image. Therefore, a line through the centre of the DFT 64 corresponds to a particular line of the sinogram (and therefore corresponds to a particular gantry angle).

The partial reconstruction circuitry 24 also receives from memory 20 (or from the CT scanner 14, or from another data store) ranges of rotation angles 66 comprising the range of rotation angles represented by imaging data set R (in this embodiment, 0° to 180°) and the range of rotation angles represented by imaging data set T (in this embodiment, 60° to 240°). The rotation angles 66 are used to determine which parts of the DFT 64 to mask out. The rotation angles 66 may also be used in reconstruction stage 56.

At stage 68, the partial reconstruction circuitry 24 creates a mask 70 for masking out a part of the DFT 64 of R that is representative of angles that are common to R and T (in this embodiment, 60° to 180°). Stage 68 may be performed before, after, or concurrently with stage 64.

The mask 70 may be used to create partial reconstructions by masking out parts of the Fourier transform of each image slice. Since each radial line through the DFT 64 corresponds to a particular line of the sinogram (CT scan data), masking out a radial line of the DFT 64 corresponds to removing the information contributed by that line of the sinogram. The masking may be considered to eliminate data for overlapping parts of a sinogram that is representative of measurements for the appropriate angles, leaving information from parts of the sinogram that contain motion information. The mask 70 may be configured to select lines passing through the origin of the DFT 74 at radial angles corresponding to a desired time period.

At stage 72, the partial reconstruction circuitry 24 applies the mask 70 to the DFT 64 of imaging data set R to obtain a masked DFT 74. The masked DFT comprises only data corresponding to measurements for angles that are included in R but are not included in T.

By applying an appropriate mask to the Fourier transform of the image R, the partial reconstruction circuitry 24 may be considered to remove information from the range of gantry rotation angles for which R and T overlap, which may leave only angles where there is motion information. Data in the range from 60° to 180° is no longer included.

At stage 76, the partial reconstruction circuitry 24 performs a two-dimensional inverse fast Fourier transform (IFFT) of the masked DFT 74 to obtain a partial reconstruction imaging data set R' (which in FIG. 5 is referred to as partial image 78).

The partial reconstruction imaging data set R' may have better temporal resolution than the imaging data set R from which it was obtained, at the expense of reduced spatial resolution in one axis. The axis having reduced spatial resolution may be an axis from which no useful motion information may have been obtained if R and T were to be registered, due to the overlap in data between R and T.

The method of FIG. 5 is also performed on imaging data set T to obtain a partial reconstruction imaging data set T', which is representative of measurements obtained for angles included in T but not in R (which in this embodiment are angles from 180° to 240°).

In other embodiments, a different method from that described above with reference to FIG. 5 may be used to obtain partial reconstruction imaging data sets R', T' from imaging data sets R, T. For example, in some embodiments, the partial reconstruction circuitry 24 performs a projection of an imaging data set, masks the resulting projection data using the rotation angles, and then performs a back-projection to obtain a partial reconstruction imaging data set. In other embodiments, any suitable method may be used. For example, in some embodiments a similar result may be achieved by convolution of the imaging data set with a highly anisotropic kernel.

Each of the partial reconstruction imaging data sets R', T' is representative of a range of angles that is less than 180° (hence the imaging data set being a partial, rather than a full, reconstruction). The angles for R' (region 30) are directly opposite the angles for T' (region 34). The angles for R' are offset by 180° from the angles for T'.

Returning to FIG. 4, the output of stage 44 is the two partial reconstruction imaging data sets R', T'. At stage 46, the partial reconstruction circuitry 24 passes the first partial reconstruction imaging data set R' to the registration circuitry 26. At stage 48, the partial reconstruction circuitry 24 passes the second partial reconstruction imaging data set T' to the registration circuitry 26.

At stage 50 of the method of FIG. 4, the registration circuitry 26 registers the first partial reconstruction imaging data set R' and the second partial reconstruction imaging data set T'. In the present embodiment, the registration circuitry 26 performs a non-rigid registration, for example by using the method of Piper, J et al, Objective evaluation of the correction by non-rigid registration of abdominal organ motion in low-dose 4D dynamic contrast-enhanced CT, Physics in Medicine and Biology 57(6), 1701-1715 (2012). A global non-rigid registration procedure is performed using Mutual Information as a similarity measure, and a warp field (deformation field) is computed using the Crum-Hill-Hawkes scheme (William R. Crum, Derek L. G. Hill, David J. Hawkes. Information Theoretic Similarity Measures in Non-rigid Registration, Proceedings of IPMI'2003, pp.378-387). In the present embodiment, the warp field is a dense vector field, in which an individual displacement vector is defined for each voxel. The warp field may be a 2D or 3D vector field representing the movement of the anatomy over a given period of time. Any other suitable registration procedure may be used in alternative embodiments.

In the present embodiment, the output of stage 50 is a warp field that represents motion between a central time point of R' and a central time point of T'. Note that the central time point of R' is not the same as the central time point of R, and the central time point of T' is not the same as the central time point of T. For example, in the case of a 90° overlap, the warp field represents motion between a point 45° before the central time point of R and a point 45° after the central time point of T (or vice versa, depending on whether R or T was scanned first).

The warp field may be considered to be representative of motion between the first scanning time period for which R is obtained and the second scanning time period for which T is obtained (taking into account that no motion information is obtained for the overlap in time between the first scanning time period and second scanning time period). The warp field may be considered to be an estimate of motion. In other embodiments, any suitable estimate of motion may be obtained from the registering of R' and T'.

At stage 52, the registration circuitry 26 passes the warp field to the image generation circuitry 28.

Although the process of FIGS. 4 and 5 is described with reference to two imaging data sets R, T and a single registration, in other embodiments there may be more instances of registration. For example, in some embodiments, there are two instances of registration, producing two warp fields that both feed into a reconstruction stage. Each instance has a different T volume with different rotation angle, but the same R.

In some previously-known methods, two or more different complete reconstructions of a single axial slice (such as, for example, imaging data sets R and T, each of which is a complete reconstruction of the same axial slice) may be registered to each other to obtain an estimate of motion occurring between a time of measurement of R and a time of measurement of T.

Different complete reconstructions of a single axial slice may be reconstructed from data obtained for overlapping scanning time periods, for example for the overlapping scanning time periods of R and T. If 360° of data is obtained for a given slice, and each complete reconstruction for that slice is reconstructed from data representative of an angular range of more than 180°, then the data used to obtain each complete reconstruction must overlap.

It may be seen from FIG. 3 that the range of angles represented by region 32 of FIG. 3 is common to imaging data sets R and T. It may be considered that there is no useful motion information to be gained by registering the data in imaging data sets R and T that is representative of the range of angles in region 32 (in this embodiment, 60° to 180°).

Therefore, in this embodiment, a first partial reconstruction R' is obtained that is representative of a range of angles that are only part of imaging data set R (and not part of imaging data set T) and a second partial reconstruction T' is obtained that is representative of a range of angles that are only part of imaging data set T (and not part of imaging data set R). The partial reconstructions from data in these ranges of angles (regions 30 and 34) may be considered to contain all the data in R and T that provides real motion information. The ranges of angles (regions 30 and 34) are consistently 180°, and therefore may be considered to represent the same spatial region.

In some circumstances, partial reconstructions R', T' may have poor (and very directional) spatial resolution, but may contain almost the same motion information as the original volumes R, T from which they were derived.

In some circumstances, a more accurate estimation of motion may be obtained by registering partial reconstructions R' and T' than may have been obtained by registering complete reconstructions R and T. Since volumes R and T are reconstructed from overlapping regions of the scan data (for example, sinogram data), parts of the volume data of R and T may be highly correlated. In some circumstances, registration of R and T may tend to over- or under-estimate motion. The over- or under-estimation of motion may depend on the orientation of image detail. The over- or under-estimation of motion may be difficult to predict. Furthermore, it may be difficult to perform a registration in the presence of motion artifacts, for example motion artifacts occurring in a complete reconstruction as shown in FIG. 1.

In some circumstances, motion estimates having increased accuracy and/or consistency may be obtained by using the method of FIG. 4. Motion may be estimated over a time period less than a temporal resolution of the volumes R, T.

An estimate of motion may be obtained without identifying any anatomical structure within the measurement volume. The estimate of motion may be obtained solely from the registration of partial reconstructions. The method of FIG. 4 may not require vessels to be tracked. The method of FIG. 4 may be performed fully automatically. Motion compensation may be applied to the entire volume instead of just to some parts of the volume, for example regions near vessels.

In some circumstances, the method of stage 4 may provide a faster method of motion estimation than is available using some previously-known methods. The method of stage 4 may achieve comparable results to some previously-known methods in a reduced time. In some circumstances, accuracy may be improved by removing confounding information that is common to both volumes R, T.

At stage 54, the image generation circuitry 28 performs a reconstruction of a data set that is representative of measurements of the measurement volume, to obtain a further imaging data set. In the process of reconstruction, the reconstruction circuitry 28 uses the estimated motion warp field 52 to compensate for motion that occurred during the capture of the measurements. The reconstruction using the estimated motion may be performed using, for example, the method of Tang et al, A combined local and global motion estimation and compensation method for cardiac CT, Proc. SPIE 9033, Medical Imaging 2014: Physics of Medical Imaging, 903304 (19 Mar. 2013).

In the present embodiment, the set of data that is reconstructed is the DFT of imaging data set T that was obtained when the process of FIG. 5 was applied to imaging data set T. In other embodiments, any suitable data may be used.

In the present embodiment, the reconstruction circuitry 28 divides the angular range of the data for imaging data set T (for example 60° to 240°) into 12 regions, each comprising a respective angular range of 15° (corresponding to a time of about 12 ms). In other embodiments, any number of regions may be used.

The reconstruction circuitry 28 obtains a respective partial reconstruction of the DFT data for each of the 12 regions, for example by using the method described above with respect to FIG. 5. Each partial reconstruction may be referred to as a partial image. Each partial image may have good spatial resolution in one direction and very poor spatial reconstruction in other directions. Each partial image may have better temporal resolution than a full reconstruction image of the DFT of T would have.

A respective time is associated with each of the partial reconstructions. For example, a partial reconstruction may be reconstructed from data representative of measurements acquired over a time period (for example, a time period of around 12 ms), and the time associated with that partial reconstruction may be a time of a midpoint of the data acquisition.

The reconstruction circuitry 28 interpolates the warp field 52 to the time associated with each of the partial reconstructions. The reconstruction circuitry 28 obtains 12 interpolated warp fields, each of which may be different.

In the present embodiment, the interpolation comprises using a cubic function with additional parameters added to adjust the interpolation. In the present embodiment, the warp field is set to zero at the middle of the target volume. In other embodiments, any method of interpolating the estimate of motion may be used.

For each of the partial reconstructions, the reconstruction circuitry 28 transforms the partial reconstruction in accordance with the interpolated warp field that was obtained by interpolating the warp field 52 to a time associated with that partial reconstruction.

The reconstruction circuitry 28 then adds together the transformed partial reconstructions to obtain the further imaging data set.

Thus, in the present embodiment, the complete reconstruction of image T is adjusted in dependence on the estimate of motion by obtaining multiple partial reconstructions of T, interpolating the warp field 52 to the different times of the different partial reconstructions, applying the interpolated warp field to transform the different partial reconstructions, and then combining the transformed partial reconstructions. By applying the estimate of motion to the reconstruction, in some cases motion effects may be reduced.

In some embodiments, the reconstruction performed at stage 54 may be a reconstruction of all the CT data obtained for a single axial slice to obtain a final image. The motion estimate of stage 52 may be used to adjust the reconstruction geometry.

At stage 56, the image generation circuitry 28 outputs the further imaging data set that has been reconstructed at stage 54.

The further imaging data set may be a data set from which some motion effects have been removed. Some motion artifacts may be reduced when compared with motion artifacts in at least one of the imaging data sets R, T. For example, fewer motion artifacts may be present in the new volumetric imaging data set than in the target phase data set T, or the severity of motion artifacts may be reduced when compared with those in target phase data set T.

The method of FIG. 4 may be performed for each axial slice in a volumetric CT data set. In some embodiments, the method of FIG. 4 may be performed for a multi-slice volume obtained from a multi-slice scanner.

For each axial slice, the computing apparatus 12 may receive any suitable number of imaging data sets. The computing apparatus 12 may obtain one or more estimates of motion by registering partial reconstructions of two or more of the imaging data sets, from which overlapping data is excluded. For each slice, the estimate or estimates of motion may be used in reconstructing a further imaging data set in which motion is compensated.

In some embodiments, the process of FIG. 4 is performed using three imaging data sets. The registration circuitry 26 determines two warp fields that feed into one final reconstruction. One of the three imaging data sets may be used as the reference (R) for both registrations, with different parts of the data masked out.

In some circumstances, motion correction performed using only two (or even one) imaging data set may provide a less detailed motion estimate than a motion correction performed using three or more imaging data sets.

In some embodiments, multiple estimates of motion may be used in reconstructing a final image. For example, different pairs of partial reconstructions may be used to obtain motion estimates for different times and/or for different angles. In some circumstances, there may be trade-offs between spatial resolution and temporal resolution that may be taken into account when deciding how many estimates to use.

In some embodiments, the CT scanner 14 reconstructs three imaging data sets (for example, T, A and B) which are received and processed by the computing apparatus 12 to obtain an estimate of motion. In other embodiments, any number of imaging data sets may be reconstructed from the volumetric CT data, each corresponding to a different time point. For example, a target phase data set and one, three, four or five reference phase data sets may be reconstructed from the CT data.

The method described above with reference to FIG. 4 may be used to produce reconstructed data sets with reduced motion artifacts. The method of FIG. 4 may provide an improved estimation of coronary artery motion. By reducing motion artifacts, it may be possible to improve image quality without increasing the speed of rotation of the CT scanner.

In some circumstances, dark shadow artifacts that may be introduced by other motion compensation methods may not be introduced in motion compensation using the method of FIG. 5. Images of vessels and/or calcifications may be improved. Dark shadow artifacts, for example dark shadows near coronary arteries, may be improved.

For some CT systems, it may be possible to obtain good quality heart images at a higher heart rate than was previously possible. It may be possible to obtain good quality heart images in a shorter scan time (and hence a lower radiation dose) than may be obtained using methods that scan for multiple heart signals. It may be possible to obtain better quality images more often, which may mean that fewer scans may need to be performed. It may be possible to scan higher heart rate patients more successfully. It may be possible to obtain better quality images at higher heart rates with the use of fewer drugs (for example, beta-blockers).

Instead of registering fully reconstructed volumes for motion estimation, partial reconstructions are created from only the data that is considered to contain useful motion information. The partial reconstructions may have better temporal resolution than fully reconstructed volumes, at the expense of spatial reconstruction in one axis. The axis for which the partial reconstructions lack spatial resolution may contain little or no useful motion information.

In the embodiment described above with reference to FIGS. 4 and 5, the computing apparatus 12 receives imaging data sets (for example, R and T), and processes the imaging data sets to obtain partial reconstruction imaging data sets (for example, R' and T').

In other embodiments, the computing apparatus 12 receives scan data (for example, CT scan data) from the scanner 14. The computing apparatus 12 selects parts of the scan data that are to be used in reconstructing partial reconstruction imaging data sets R', T'. In some embodiments, the computing apparatus 12 reconstructs partial reconstruction imaging data sets R', T' without first performing any complete reconstruction (for example, without reconstructing imaging data sets R, T).

Referring again to the exemplary angles of FIG. 3, in one embodiment the partial reconstruction circuitry 24 receives a set of scan data, and selects a portion of the scan data comprising measurements obtained in angular range 30 (0° to 60°). The scan data in angular range 30 is data that was obtained during a first scanning time period (the time taken to scan from 0° to 180°) but not during a second scanning time period (the time taken to scan from 60° to 240°). The partial reconstruction circuitry 24 reconstructs a partial reconstruction imaging data set R' from the selected portion of the scan data.

The reconstruction circuitry 24 selects a portion of the scan data comprising measurements obtained in angular range 34 (180° to 240°). The scan data in angular range 30 is data that was obtained during a second scanning time period (the time taken to scan from 60° to 240°) but not during a first scanning time period (the time taken to scan from 0° to 180°). The partial reconstruction circuitry 24 reconstructs a partial reconstruction imaging data set T' from that selected portion of the scan data.

The registration circuitry 26 obtains an estimate of motion from the partial reconstruction imaging data sets R', T' and the image generation circuitry 28 reconstructs an imaging data set that is a complete reconstruction of scan data for the axial slice, for example using the method described above with reference to FIG. 4.

In further embodiments, the scanner reconstruction circuitry 15 of the scanner 14, instead of the partial reconstruction circuitry 24, reconstructs parts of the scan data to obtain the partial reconstruction imaging data sets R', T'. In some embodiments, the scanner 14 passes the partial reconstruction imaging data sets to computing apparatus 12. In further embodiments, some or all of the process of FIG. 4 is performed in the scanner 14 or in any suitable apparatus.

In the present embodiment, the scanner acquires CT data and reconstructs that CT data to provide imaging data. In other embodiments, the scanner acquires data of any suitable modality (for example, CT, cone-beam CT, MR, PET, SPECT, X-ray or ultrasound) and uses a reconstruction method suitable for reconstructing imaging data sets from data of the acquired modality. The scanner may reconstruct data from the scanner to provide any appropriate two-dimensional or three-dimensional imaging data sets. In some embodiments, the scanner is a hybrid scanner (for example, a CT-MR or CT-PET scanner) and the method of FIG. 2 is applied to the CT portion of data from the hybrid scanner.

In some embodiments, the scanner is a cone-beam CT scanner. In some embodiments, the imaging data sets are angiography imaging data sets. Cone-beam CT may have a slower rotation speed than some other CT scan methods. In some circumstances, a cone-beam CT scanner may experience some unwanted movement (for example a wobbling movement) during rotation. In some cone-beam CT embodiments, more than two registrations are performed when estimating motion, to obtain a more detailed model of movement over time.

The measurement volume may be any appropriate anatomical region of any human or animal subject, for example the abdominal region. The anatomical region may comprise any suitable anatomical structure, for example any organ (for example, heart, brain, lung or liver) or vessel (for example, coronary artery).

Certain embodiments may provide a medical imaging method comprising: receiving two 2D or 3D CT image datasets of a given portion of a patient, each dataset reconstructed from sinogram data over a given time period, such that the time periods of the two datasets overlap; for each image dataset, determining the range of time periods that do not overlap with the time period of the other dataset; computing a partial reconstruction of each image dataset, containing only information that is not shared with the other dataset; and registration of the resulting partial reconstructions, to obtain an estimate of motion between the two image datasets.

The computing of the partial reconstruction may comprise computing the 2D Fourier transformation (DFT) of each image of each dataset; applying a mask that selects only lines passing through the origin of each DFT image at radial angles corresponding to the non-overlapping time period; and computing the 2D inverse DFT of the resulting masked images.

At least one of the datasets may be affected by motion artifacts. The portion of the patient may be a heart.

Certain embodiments may provide a medical imaging method comprising receiving at least two CT image datasets of a given portion of a patient, with one referred to as the target phase; registering each dataset except the target phase against the target phase dataset, and obtaining a set of motion fields encoding patient movement; and based on the motion fields and the original image datasets, reconstructing a further image dataset that is less affected by motion artifacts.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging data processing apparatus, comprising processing circuitry configured to:
    obtain a first image reconstructed from measurements of a measurement volume obtained by rotation of a medical scanner relative to the measurement volume during a first scanning time period;
    obtain a second image reconstructed from measurements of the measurement volume obtained by rotation of the medical scanner relative to the measurement volume during a second scanning time period that overlaps the first scanning time period; and
    perform a procedure to obtain an estimate of motion between the first scanning time period and second scanning time period based on the first image and the second image, the procedure comprising:
    processing the first image to obtain first processed data that is representative of the measurements obtained during the first scanning time period;
    applying a first mask to the first processed data to mask out a part of the first processed data that is representative of measurements obtained during an overlap between the first scanning time period and the second scanning time period;
    obtaining a first partial reconstruction by reconstructing a remaining part of the first processed data after the first mask has been applied;
    processing the second image to obtain second processed data that is representative of the measurements obtained during the second scanning time period;
    applying a second mask to the second processed data to mask out a part of the second processed data that is representative of measurements obtained during the overlap between the first scanning time period and the second scanning time period;
    obtaining a second partial reconstruction by reconstructing a remaining part of the second processed data after the second mask has been applied,
    such that each of the partial reconstructions is reconstructed from data corresponding to a respective less than 180 degrees of rotation of the medical scanner; and
    performing a motion estimation based on the first partial reconstruction and the second partial reconstruction to obtain the estimate of motion;
    wherein a data set representative of measurements obtained during at least one of the first scanning time period and second scanning time period is suitable for use in reconstructing a medical imaging data set representative of at least part of the measurement volume.

2. An apparatus according to claim 1, wherein the estimate of motion comprises a warp field.

3. An apparatus according to claim 1, wherein the processing circuitry is further configured to reconstruct a medical imaging data set from the data set representative of measurements obtained during at least one of the first scanning time period and second scanning time period.

4. An apparatus according to claim 3, wherein the reconstructing of the medical imaging data set is in dependence on the estimate of motion.

5. An apparatus according to claim 3, wherein the reconstructing of the medical image data sets comprises:

obtaining a plurality of partial reconstructions of regions of the data set, each representative of a different time period;

interpolating the estimate of motion to each of the different time periods; and applying to each of the partial reconstructions the interpolated estimate of motion for the corresponding time period.

6. An apparatus according to claim 1, wherein the obtaining of the first image comprises processing a first medical imaging data set reconstructed from measurements obtained during the first scanning time period, and the obtaining of the second image comprises processing a second medical imaging data set reconstructed from measurements obtained during the second scanning time period.

7. An apparatus according to claim 6, wherein the processing of each of the first medical imaging data set and the second medical imaging data set comprises at least one of: performing a Fourier transform, performing a projection, convolution with a highly anisotropic kernel.

8. An apparatus according to claim 6, wherein the processing of each of the first medical imaging data set and second medical imaging data set comprises removing data representative of measurements obtained during the overlap between the first scanning time period and the second scanning time period.

9. An apparatus according to claim 1, wherein the obtaining of the first and second images comprises:
obtaining a scan image comprising measurements representative of measurements obtained during both the first and the second scanning time periods; and
excluding measurements obtained during the overlap between the first scanning time period and second scanning time period.

10. An apparatus according to claim 1 wherein, for each of the first and second scanning time periods, a rotation of the medical scanner during that scanning time period comprises a rotation of at least 180°.

11. An apparatus according to claim 1, wherein the first scanning time period and second scanning time period both occur during a single rotation of the medical scanner.

12. An apparatus according to claim 1, wherein the first image is representative of measurements obtained for a first portion of a rotation, the second image is representative of measurements obtained for a second portion of the rotation and at least one of a), b) and c):—
a) each of the first portion and second portion occupies a respective less than 180° of rotation, optionally less than 90°;
b) the first portion and second portion are of the same size;
c) the first portion and second portion are offset by 180°.

13. An apparatus according to claim 1, wherein each of the first image and second image comprises a respective plurality of data subsets, wherein each data subset is representative of measurements obtained at a different scanning time.

14. An apparatus according to claim 1, wherein each of the first image and second image comprises at least one of projection data, sinogram data.

15. A medical imaging data processing method, comprising:
obtaining a first image reconstructed from measurements of a measurement volume obtained by rotation of a medical scanner relative to the measurement volume during a first scanning time period;
obtaining a second image reconstructed from measurements of the measurement volume obtained by rotation of the medical scanner relative to the measurement volume during a second scanning time period that overlaps the first scanning time period; and
performing a procedure to obtain an estimate of motion between the first scanning time period and second scanning time period based on the first image and the second image, the procedure comprising:
processing the first image to obtain first processed data that is representative of the measurements obtained during the first scanning time period;
applying a first mask to the first processed data to mask out a part of the first processed data that is representative of measurements obtained during an overlap between the first scanning time period and the second scanning time period;
obtaining a first partial reconstruction by reconstructing a remaining part of the first processed data after the first mask has been applied;
processing the second image to obtain second processed data that is representative of the measurements obtained during the second scanning time period;
applying a second mask to the second processed data to mask out a part of the second processed data that is representative of measurements obtained during the overlap between the first scanning time period and the second scanning time period;
obtaining a second partial reconstruction by reconstructing a remaining part of the second processed data after the second mask has been applied,
such that each of the partial reconstructions is reconstructed from data corresponding to a respective less than 180 degrees of rotation of the medical scanner; and
performing a motion estimation based on the first partial reconstruction and the second partial reconstruction to obtain the estimate of motion;
wherein a data set representative of measurements obtained during at least one of the first scanning time period and second scanning time period is suitable for use in reconstructing a medical imaging data set representative of at least part of the measurement volume.

16. A method according to claim 15, comprising reconstructing a medical imaging data set from the data set representative of measurements obtained during at least one of the first scanning time period and second scanning time period.

17. A method according to claim 16, wherein the reconstructing of the medical image data sets comprises:
obtaining a plurality of partial reconstructions of regions of the data set, each representative of a different time period;
interpolating the estimate of motion to each of the different time periods; and
applying to each of the partial reconstructions the interpolated estimate of motion for the corresponding time period.

18. A method according to claim 15, wherein the obtaining of the first image comprises processing a first medical imaging data set reconstructed from measurements obtained during the first scanning time period, and the obtaining of the second image comprises processing a second medical imaging data set reconstructed from measurements obtained during the second scanning time period.

19. A method according to claim 18, wherein the processing of each of the first medical imaging data set and second medical imaging data set comprises removing data representative of measurements obtained during the overlap between the first scanning time period and the second scanning time period.

20. A method according to claim 15, wherein the first scanning time period and second scanning time period both occur during a single rotation of the medical scanner.

* * * * *